United States Patent [19]

Sandy

[11] 4,189,306
[45] Feb. 19, 1980

[54] HEXACOORDINATED TRANSITION METAL COMPOUNDS AND FUEL COMPOSITIONS CONTAINING THEM

[75] Inventor: Charles A. Sandy, Wilmington, Del.

[73] Assignee: E. I. Du Pont de Nemours and Company, Wilmington, Del.

[21] Appl. No.: 948,582

[22] Filed: Oct. 4, 1978

[51] Int. Cl.² .............................................. C10L 1/30
[52] U.S. Cl. .................................. 44/68; 260/429 R; 260/429 J; 260/439 R
[58] Field of Search ................. 44/68, 63; 260/429 R, 260/429 J, 439 R

[56] References Cited

U.S. PATENT DOCUMENTS

| | | | |
|---|---|---|---|
| 2,086,775 | 7/1937 | Lyons et al. | |
| 2,144,654 | 1/1939 | Guthmann et al. | |
| 2,156,918 | 5/1939 | Lyons | |
| 2,235,466 | 3/1941 | van Peski et al. | |
| 2,737,932 | 3/1956 | Thomas | |
| 2,902,983 | 9/1959 | Patberg | |
| 2,926,184 | 2/1960 | Irish et al. | 260/439 R |
| 3,157,682 | 11/1964 | Ramsden | 260/429 J |
| 3,326,949 | 6/1967 | Larson | 260/429 J |
| 3,459,703 | 8/1969 | Briggs et al. | 260/439 R |
| 3,474,464 | 10/1969 | Matthews et al. | 260/439 R |
| 3,562,308 | 2/1971 | Costa et al. | 260/439 R |
| 3,594,216 | 7/1971 | Charles et al. | 260/439 R |
| 4,008,260 | 2/1977 | Kunstle | 260/439 R |

FOREIGN PATENT DOCUMENTS

287192 3/1928 United Kingdom.

OTHER PUBLICATIONS

Fackler et al., Inorg. Chem. 6, 921 (1965).
Graddon, Cord. Chem. Rev., 4, 1 (1969).
Graddon, Nature 195, 891 (1961), "Polymerization of Transition Metal Beta-Diketone Chelates".
Cotton and Elder, J. Am. Chem. Soc., 86, 2294 (1964), "The Tetrameric Structure of Anhydrous Crystalline Colbalt (II) Acetylacetonate".
Hammond et al., Inorg. Chem. 2, 75 (1963).
Gerlach et al., Inorg. Chem. 8, pp. 2293 and 2294 (1969).
Biltz Zert. Anorg. Chem. 40, 221 (1904).
Morgan et al., J. Chem. Soc. 105, 192 (1914).

*Primary Examiner*—Winston A. Douglas
*Assistant Examiner*—Y. Harris-Smith
*Attorney, Agent, or Firm*—James A. Costello

[57] ABSTRACT

Hexacoordinated transition metal compounds and fuel compositions containing them, said compounds represented by the structure

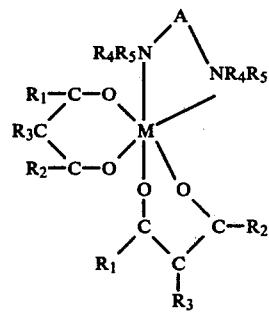

wherein:
M is selected from at least one member of the group Mn, Fe, Co and Ni,
$R_1$ and $R_2$ are hydrocarbyl groups of 1 to 6 carbon atoms,
$R_3$ is hydrogen or an alkyl of 1 to 6 carbon atoms,
$R_4$ and $R_5$ are hydrogen or alkyl of 1 to 4 carbon atoms, and
A is a divalent hydrocarbyl group of 2 to 10 carbon atoms selected from a member of the group alkylene, phenylene and cycloalkylene, each member providing 2 or 3 carbon atoms between the nitrogen atoms with the proviso that when A is phenylene the number of carbon atoms between the nitrogen atoms is 2.

10 Claims, No Drawings

HEXACOORDINATED TRANSITION METAL COMPOUNDS AND FUEL COMPOSITIONS CONTAINING THEM

BACKGROUND OF THE INVENTION

This invention concerns hexacoordinated compounds of Mn, Fe, Co and Ni, and fuel compositions containing them.

The octane quality of a fuel is an important indication of the power, efficiency and economy the fuel will deliver to internal combustion engines which run on it. One way to increase the octane quality of a fuel is to increase the amount therein of high octane hydrocarbon components such as benzene, toluene and the like. An alternate way to increase octane quality is to incorporate antiknock additives into the fuels.

In the past, tetraalkyllead compounds were regularly used by refiners as an additive to increase octane quality. With the advent of automobiles equipped with catalytic converters for exhaust emission control purposes has come the attendant requirement for lead-free gasolines. The alternative of increasing the high octane hydrocarbon components of the fuel is not particularly acceptable for improving octane quality, such components being more valuable when used as solvents or petrochemical feedstocks.

Nonlead antiknock additives, both metal-containing and metal-free, have been suggested as replacements for tetraalkyllead antiknocks. These additives have not attained widespread use because of one or more deficiencies in their antiknock activity, hydrolytic or oxidative stabilities or fuel solubility. Accordingly, there is a need for effective and stable nonlead additives to improve fuel octane ratings.

Certain metal (nonlead) beta-diketone compounds have been suggested as antiknock additives for hydrocarbon fuels. Said beta-diketone compounds have low fuel solubility and low volatility, however, and have not been used commercially. See British Pat. No. 287,192 and U.S. Pat. Nos. 2,114,654 and 2,156,918.

Studies such as the following: Graddon, Nature 195, 891 (1961), "Polymerization of Transition Metal Beta-Diketone Chelates,"; Cotton and Elder, J. Am. Chem. Soc., 86, 2294 (1964) "The Tetrameric Structure of Anhydrous Crystalline Cobalt (II) Acetylacetonate"; and Graddon, Cord. Chem. Rev., 4, 1 (1969), indicate that the tetracoordinated acetylacetonates of Mn, Fe, Co, and Ni are polymerized (trimers and tetramers) in the solid state and in nonpolar solvents. The oligomeric nature of these compounds most probably explains their low solubility in gasolines and their low volatility.

It is known to prepare divalent transition metal chelates of beta-diketones which are monomeric in the solid state and in nonpolar solvents by using a beta-diketone with bulky groups such that the steric contributions of the bulky groups in the chelate compounds preclude self-polymerization of the chelate compounds. Thus, chelate compounds of divalent transition metals with 2,2,6,6-tetramethyl-3,5-heptanedione (dipivaloylmethane, DPM) are reported to be monomeric in the solid state and in nonpolar solvents. However, while the presence of bulky groups in beta-diketone provide monomeric chelate compounds, such compounds are not practical for most uses because of their great sensitivity to air oxidation. For instance, Fe(DPM)$_2$ is reported to "char immediately on exposure to air", Fackler et al., Inorg. Chem., 6, 921 (1965); Mn(DPM)$_2$ "charred immediately on contact with air", Hammond et al., Inorg. Chem., 2, 75 (1963); and there is extreme sensitivity of Co(DPM)$_2$ to oxidation, Hammond, supra, page 76, and Gerlach et al., Inorg. Chem., 8, pp. 2293 and 2294 (1969).

SUMMARY OF THE INVENTION

This invention concerns hexacoordinated transition metal compounds represented by the formula

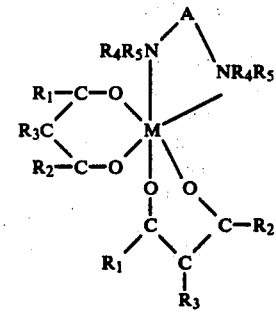

wherein:
M is selected from at least one member of the group Mn, Fe, Co and Ni,
R$_1$ and R$_2$ are hydrocarbyl groups of 1 to 6 carbon atoms,
R$_3$ is hydrogen or an alkyl of 1 to 6 carbon atoms,
R$_4$ and R$_5$ are hydrogen or alkyl of 1 to 4 carbon atoms, and
A is a divalent hydrocarbyl group of 2 to 10 carbon atoms selected from a member of the group alkylene, phenylene and cycloalkylene, each member providing 2 or 3 carbon atoms between the nitrogen atoms with the proviso that when A is phenylene the number of carbon atoms between the nitrogen atoms is 2.

The preferred compounds of this invention are the following: (i) that wherein R$_1$=R$_2$=CH$_3$, R$_3$=H, R$_4$=R$_5$=CH$_3$ and A is —CH$_2$—CH$_2$—, (ii) that wherein R$_1$=CH$_3$, R$_2$=—CH$_2$CH(CH$_3$)$_2$, R$_3$=H, R$_4$=R$_5$=CH$_3$ and A is —CH$_2$CH$_2$—, (iii) that wherein R$_1$=R$_2$=—C(CH$_3$)$_3$, R$_3$=H, R$_4$=R$_5$=CH$_3$ and A is —CH$_2$CH$_2$—, and (iv) that wherein M is divalent cobalt or nickel, especially cobalt. The fuel compositions of this invention comprise hydrocarbons boiling in the gasoline boiling range and an octane-improving amount of the hexacoordinated antiknock compounds described herein.

DETAILS OF THE INVENTION

The compounds of this invention are prepared by contacting a water-soluble divalent metal salt of manganese, iron, cobalt or nickel (such as the chlorides, nitrates, acetates and the like), a beta-diketone, and a diamine ligand, in the molar ratio of about 1:2:1 in the presence of aqueous alkali. Little or no heating is required. The reaction can be carried out under an inert gas atmosphere but an inert atmosphere is not required. Thus, for example, Cobalt (II) dichloride, acetylacetone (AA), and tetramethylethylenediamine (TMED) are contacted in the presence of aqueous sodium hydroxide to form Co(II)(AA)$_2$.TMED as a precipitate which can be easily isolated by filtration.

The beta-diketones suitable for the preparation of compounds of the invention are represented by the formula

where $R_1$, $R_2$ and $R_3$ are as defined. It is necessary that the carbon atom between the two carbonyl groups have at least one hydrogen substituent. The abstraction of this hydrogen by the base provides a beta-diketone anion which chelates with the metal ion present. $R_1$ and $R_2$ are hydrocarbyl groups of 1 to 6 carbon atoms and include alkyl, alkenyl and phenyl groups. Preferred alkyl groups are methyl, ethyl, propyl, butyl, amyl and hexyl, both normal chains and branched chains. When $R_3$ is an alkyl group of 1 to 6 carbon atoms, it will be selected from methyl, ethyl, propyl, butyl, amyl and hexyl, both normal and branched chain. Beta-diketones are well-known in the art, some are available commercially, and all are readily prepared by art-known methods.

The preferred compounds are prepared from beta-diketones wherein $R_1$ and $R_2$ represent alkyl groups of 1 to 4 carbon atoms and $R_3$ represents hydrogen. More specifically, the preferred beta-diketones are 2,4-pentanedione, 3-methyl-2,4-pentanedione, 3-isopropyl-2,4-pentanedione, 2,4-hexanedione, 2-methyl-3,5-hexanedione, 3-methyl-3,5-heptanedione, 3,5-heptanedione, 2,6-dimethyl-3,5-heptanedione, 2-methyl-4,6-heptanedione, 2-methyl-4,6-octanedione, 2,8-dimethyl-4,6-nonanedione, and 2,2,6,6-tetramethyl-3,5-heptanedione.

The diamine ligand is represented by

where $R_4$, $R_5$ and A are as defined. The provision in the hydrocarbyl group, A, of 2 to 3 carbon atoms between the nitrogen atoms is important to provide increased stability by the formation of a 5 to 6 membered ring upon chelation of the diamine with the metal ion. The amine ligand must be a diamine since a monoamine does not afford a compound of sufficient stability. The hydrocarbyl group, A, can be an alkylene group such as ethylene and propylene or an alkyl-substituted ethylene or propylene group or a cycloalkylene or a phenylene group such as 1,2-phenylene. The $R_4$ and $R_5$ substituents on the nitrogen atoms can be either hydrogen or alkyls of 1 to 4 carbon atoms and thus in the diamine, each of the amino group can be a primary, secondary or teritary amino group. Representative diamines include ethylenediamine, 1,2-propylenediamine, 1,3-propylenediamine, 2-methyl-1,3-diaminepropane, 2,2-dimethyl-1,3-diaminopropane, ortho-phenylenediamine and the corresponding 1 to 4 carbon alkyl-substituted diamines.

Representative methyl substituted diamines are as follows:
N-methylethylenediamine,
N,N-dimethylethylenediamine,
N,N'-dimethylethylenediamine,
N,N,N'-trimethylethylenediamine,
N,N,N',N'-tetramethylethylenediamine,
N-methyl-1,2-propylenediamine,
N,N-dimethyl-1,2-propylenediamine,
N,N'-dimethyl-1,2-propylenediamine,
N,N,N'-trimethyl-1,2-propylenediamine,
N,N,N',N'-tetramethyl-1,2-propylenediamine,
N-methyl-1,3-propylenediamine,
N,N-dimethyl-1,3-propylenediamine,
N,N'-dimethyl-1,3-propylenediamine,
N,N,N'-trimethylpropylenediamine,
N,N,N',N'-tetramethyl-1,3-propylenediamine,
N-methyl-2-methyl-1,3-diaminopropane,
N,N-dimethyl-2-methyl-1,3-diaminopropane,
N,N'-dimethyl-2-methyl-1,3-diaminopropane,
N,N,N'-trimethyl-2-methyl-1,3-diaminopropane,
N,N,N',N'-tetramethyl-2-methyl-1,3-diaminopropane,
N-methyl-2,2-dimethyl-1,3-diaminopropane,
N,N-dimethyl-2,2-dimethyl-1,3-diaminopropane,
N,N'-dimethyl-2,2-dimethyl-1,3-diaminopropane,
N,N,N'-trimethyl-2,2-dimethyl-1,3-diaminopropane,
N,N,N',N'-tetramethyl-2,2-dimethyl-1,3-diaminopropane,
N-methyl-o-phenylenediamine,
N,N-dimethyl-o-phenylenediamine,
N,N'-dimethyl-o-phenylenediamine,
N,N,N'-trimethyl-o-phenylenediamine,
N,N,N',N'-tetramethyl-o-phenylenediamine and the like. The preferred methyl substituted diamines include
N,N,N',N'-tetramethylethylenediamine,
N,N,N',N'-tetramethyl-1,2-propylenediamine,
N,N,N',N'-tetramethyl-1,3-propylenediamine, and
N,N,N',N'-tetramethyl-2,2-dimethyl-1,3-diaminopropane.

It should be understood that representative diamines include those set out above wherein all or some of the methyl substituents is replaced by one or more of ethyl, propyl or butyl substituents.

The compounds of the invention are monomeric, soluble in hydrocarbons, volatile and stable. The compounds were demonstrated to be monomeric in benzene solution by cryoscopic determinations of molecular weight. In the present context, "soluble" means having sufficient solubility in hydrocarbon fuels such as gasoline to provide concentrations of at least 0.01 gram of metal per gallon; "volatile" means substantially complete volatilization by about 250° C. of about 20 mg of the compound when heated, as determined by Thermal Gravimetric Analysis (TGA) under conditions of heating at the rate of 5° C./minute with nitrogen gas passed over the sample at the rate of 40 cc/minute; and "stable" means resistant to oxidation upon exposure to air.

The hydrocarbon fuels to which the compounds are added comprise hydrocarbons boiling in the gasoline boiling range which range is normally about 20° C. to 225° C. The base fuel can consist of straight-chain or branched-chain paraffins, cycloparaffins, olefins and aromatic compounds or any mixture of such hydrocarbons obtainable from straight run naphtha, polymer gasoline, natural gasoline, thermally or catalytically cracked hydrocarbon stocks and catalytically reformed stocks. The gasoline may also contain conventional gasoline additives such as antiknock compounds, dyes, antioxidants, anti-icing agents, rust inhibitors, detergents, anti-preignition agents, stabilizers, intake valve deposit control additives and the like.

The amount of the compound to be incorporated into gasoline to improve its antiknock quality will depend upon the antiknock quality of the base gasoline itself and the improvements desired. In normal practice a refiner obtains the desired gasoline antiknock quality by the combination of hydrocarbon feed processing and the use of antiknock additives consistent with economy. The instant compounds provide antiknock improvements when used in the amount needed to provide about 0.01 gram of metal per gallon and can be used in an amount to provide up to 10 grams of metal per gallon. Preferably, the metal concentration will be from about 0.02 to 3 grams of metal per gallon, more preferably from about 0.025 to 0.5 gram of metal per gallon.

The compounds of the present invention do not all exhibit the same degree of stability or volatility. All the compounds are, however, monomeric, stable to air, and soluble in most organic solvents including such nonpolar solvents as hydrocarbons. Since volatility is an important property for antiknock activity, the preferred compounds for antiknock utility will have less than about 35 carbon atoms. Of course, the number of carbon atoms is not so important when utility does not depend upon volatility.

Oxidative stability of the compounds in hydrocarbon fuels depends upon the nature of the hydrocarbon fuel, the particular metal present in the compound and the beta-diketone ligand used to prepare the compound. It has been found that compounds containing beta-diketone ligands with branched alkyl groups have better solution stability than compounds with straight chain alkyl groups in the beta-diketone ligands.

Regardless of the nature of the fuel in which they are used, the cobalt and nickel compounds will have better oxidative stability than the manganese and iron compounds. In fact, fuels which contain manganese and/or iron compounds should be used relatively quickly before compound oxidation. Generally, alkanes and cycloalkanes such as hexane, isooctane, cyclopentane and cyclohexane are most conducive to the formation of oxidatively stable solutions. On the other hand, the compounds of the invention tend to undergo oxidation reactions in olefin-containing solvents.

In addition to their utility an antiknock additives, the compounds of the invention are useful as octane requirement increase control additives when added in the fuel and/or the crankcase lubricant. Another utility is to control the formation of carbon resulting from combustion of gasolines and fuel oils. The compounds can also be employed as colorants in organic systems including hydrocarbon fuels.

The following Examples illustrate the invention. Thermogravimetric analyses following the preparative details indicate the good volatility and thermal and oxidative stabilities of the compounds of this invention. The analyses were carried out on a Du Pont 990 Thermal Analyzer coupled to a Du Pont 951 Thermogravimetric Analyzer. In each characterization, approximately 20 mg of the sample was heated over a temperature range of 25° to 500° C. at a heating rate of 5° C. per minute with either nitrogen or air as the carrier gas at a gas flow rate of 40 ml per minute. The loss in sample weight with increasing temperature was recorded continuously. Thermal or oxidative instability is ordinarily indicated by a discontinuous loss in weight followed by little or no loss in weight since the metal residue from thermal or oxidative decomposition is not volatile. It will be noted that in each of the following analyses, employing nitrogen or air as the carrier gas, the loss in sample weight with increasing temperature is smooth and continuous.

EXAMPLE 1

Preparation of Bis(acetylacetonato)cobalt(II)tetramethylethylenediamine, Co(II)(AA)$_2$.TMED, wherein $R_1=R_2=CH_3$; $R_3=H$; $R_4=R_5=CH_3$; and $A=-CH_2-CH_2-$.

To a 5-liter reaction flask equipped with mechanical agitation, a condenser, a gas inlet tube and an addition funnel, 3000 ml of deionized water was added. The water was sparged for ½ hour with nitrogen. Then, 238 g of CoCl$_2$.6H$_2$O was added to the reaction flask followed by addition of 200 g of 2,4-pentanedione (acetylacetone, AA) and 140 g of N,N,N',N'-tetramethylethylenediamine (TMED). Upon addition of TMED, a fine pink precipitate formed. A solution of sodium hydroxide (80 g in 700 ml of water) was then added over a period of 1½ hours during which addition, the pink-orange precipitate changed to larger blue-red precipitate. The reaction mixture was stirred for about 1½ hours following the sodium hydroxide addition and then filtered.

The precipitate collected by filtration was washed with water, then was dissolved in 1500 ml of toluene at room temperature by stirring for 1½ to 2 hours. The toluene solution was filtered and dried over anhydrous sodium sulfate. Toluene was then removed by stripping at 90° to 95° C. at 20 to 30 mm pressure. The liquid residue was poured into an enamel pan to cool. The cooled product solidified and was broken up and ground, m.p. 90.5° to 91.5° C. The yield of Co(II)-(AA)$_2$.TMED was 315 g. The compound was stable in air, soluble in hydrocarbon fuel and monomeric in benzene as determined by cryoscopic method. Elemental analysis: Calculated for Co(C$_{16}$H$_{30}$N$_2$O$_4$): C, 51.4; H, 8.0; N, 7.5; Co, 16.0. Found: C, 51.3; H, 7.9; N, 7.8; Co, 15.8.

EXAMPLE 2

A mixture of 25.7 g of commercially available bis-(acetylacetonato)cobalt(II) and 50 ml of dimethylformamide was stirred in a 250 ml reaction flask equipped with an agitator, a thermometer, a reflux condenser and an addition funnel for 50 minutes, then 11.6 g of N,N,N',N'-tetramethylethylenediamine was added, and the temperature rose about 4° C. An additional 100 ml of dimethylformamide was added and the mixture was filtered to remove a small amount (less than 1 g) of insoluble material. Dimethylformamide was removed under reduced pressure of 11 to 15 mm in the temperature range of 58° to 62° C. The residue was dried on a porous plate to yield 31.3 g (81.8% yield) of bis-(acetylacetonato)cobalt(II) tetramethylethylenediamine addition product which melted in the range of 90° to 92° C. The following elemental analyses were obtained: C, 51.5; H, 7.5; N, 7.4; and Co, 16.0 while the theoretical values for the compound are C, 51.4; H, 8.0; N, 7.5; and Co, 16.0.

| Thermogravimetric Analysis Co(II) (AA)$_2$ . TMED | | | |
|---|---|---|---|
| Carrier Gas = Nitrogen Sample Wt. 17.0 mg | | Carrier Gas = Air Sample Wt. 17.2 mg | |
| Temp. (°C.) | Wt. % Volatilized | Temp. (°C.) | Wt. % Volatilized |
| 85 | 0 | 90 | 0 |
| 95 | 0.3 | 100 | 0.3 |
| 110 | 1.2 | 115 | 2.3 |
| 120 | 1.8 | 127 | 4.7 |
| 125 | 2.9 | 140 | 9.3 |
| 135 | 5.3 | 155 | 18.6 |
| 145 | 8.2 | 162 | 24.4 |
| 150 | 10.6 | 168 | 30.2 |
| 160 | 16.5 | 175 | 38.4 |
| 170 | 24.7 | 182 | 47.7 |
| 175 | 30.6 | 186 | 53.5 |

-continued

Thermogravimetric Analysis
Co(II) (AA)$_2$ . TMED

| Carrier Gas = Nitrogen Sample Wt. 17.0 mg | | Carrier Gas = Air Sample Wt. 17.2 mg | |
|---|---|---|---|
| Temp. (°C.) | Wt. % Volatilized | Temp. (°C.) | Wt. % Volatilized |
| 185 | 44.7 | 190 | 59.3 |
| 195 | 62.3 | 200 | 74.4 |
| 200 | 72.3 | 205 | 82.6 |
| 205 | 82.3 | 210 | 87.2 |
| 210 | 90.6 | 215 | 89.5 |
| 215 | 94.1 | Decomposition | |
| 217 | 95.9 | | |
| Decomposition | | | |

EXAMPLE 3

Preparation of Bis(isovalerylacetonato)Co(II)tetramethylethylenediamine, Co(II)(IVA)$_2$.TMED, wherein $R_1$=CH$_3$; $R_2$=CH$_2$—CH(CH$_3$)$_2$; $R_3$=H; $R_4$=$R_5$=CH$_3$; A=—CH$_2$—CH$_2$—.

In a 3-liter reaction flask equipped with an agitator, a thermometer, a condenser and an addition funnel, 1000 ml of toluene and 229 g of bis(isovalerylacetonato)-cobalt(II)(Co(II)(IVA)$_2$) were mixed. To the mixture was added 78 g of N,N,N',N'-tetramethylethylenediamine (TMED) over 12 minutes. The mixture was stirred for about 1 hour and filtered. The filtrate was washed twice with 275 ml of water. The toluene solution was dried over anhydrous calcium sulfate, and filtered. The removal of toluene at 50° to 75° C. under reduced pressure provided 254.5 g of red-brown viscous oil (92% yield) of the product. The compound was stable in air, soluble in hydrocarbons and monomeric in benzene as determined cryoscopically. Elemental analysis: Calculated for Co(C$_{22}$H$_4$N$_2$O$_4$): C, 57.8; H, 9.3; N, 6.1; Co, 12.9. Found: C, 58.5; H, 9.3; N, 6.6; Co, 13.0.

Thermogravimetric Analysis
Co(II) (IVA)$_2$ . TMED

| Carrier Gas = Nitrogen Sample Wt.17.18 mg | | Carrier Gas = Air Sample Wt. 18.6 mg | |
|---|---|---|---|
| Temp. (°C.) | Wt. % Volatilized | Temp. (°C.) | Wt. % Volatilized |
| 25 | 0 | 100 | 0 |
| 50 | 0.5 | 125 | 1.6 |
| 75 | 1.0 | 135 | 3.2 |
| 100 | 1.3 | 150 | 6.5 |
| 125 | 1.6 | 160 | 9.7 |
| 140 | 4.6 | 170 | 14.0 |
| 150 | 7.4 | 175 | 16.7 |
| 160 | 10.9 | 185 | 23.7 |
| 170 | 16.2 | 190 | 28.0 |
| 190 | 33.6 | 200 | 38.7 |
| 200 | 46.4 | 210 | 50.5 |
| 205 | 54.6 | 215 | 57.0 |
| 210 | 63.3 | 225 | 69.9 |
| 215 | 72.1 | 234 | 78.5 |
| 220 | 80.2 | 240 | 81.2 |
| 225 | 87.2 | Decomposition | |
| 230 | 92.4 | | |
| 235 | 95.3 | | |
| Decomposition | | | |

EXAMPLE 4

Preparation of Bis(dipivaloylmethanato)Co(II)tetramethylethylenediamine, Co(II)(DPM)$_2$.TMED, wherein $R_1$=$R_2$=C(CH$_3$)$_3$; $R_3$=H; $R_4$=$R_5$=CH$_3$; A=—CH$_2$—CH$_2$—.

Into a 250 ml reaction flask equipped with an agitator, a thermometer, a condenser and an addition funnel, was added 100 ml of denatured ethyl alcohol. Anhydrous CoCl$_2$ (13 g) was then added and the mixture was stirred (temperature rise of 9° C.). Then a solution of 37 g of 2,2,6,6-tetramethyl-3,5-heptanedione (dipivaloylmethane, DPM) and 11.6 g of N,N,N',N'-tetramethylethylenediamine (TMED) was added over a period of one hour and five minutes (temperature rise of 5° C.), providing a finely divided blue precipitate. After stirring the mixture for ½ hour, a solution of 8 g of sodium hydroxide in 25 ml of distilled water was added over a period of 1 hour (temperature rise of 6° C.). The precipitate changed in color to bronze. The reaction mixture was stirred for an additional 1½ hours and filtered. The precipitate was washed with water and dried in air. Yield of Co(II)(DPM)$_2$.TMED was 49 g (90.5% of theory). The compound melted at 236° to 237° C. The compound was stable in air, soluble in hydrocarbons and monomeric in benzene as determined cryoscopically. Elemental analysis: Calculated for Co(C$_{28}$H$_{54}$N$_2$O$_4$): C, 62.1; H, 10.0; N, 5.2; Co, 10.9. Found: C, 62.2; H, 9.8; N, 5.3; Co, 10.9.

Thermogravimetric Analysis
Co(II) (DPM)$_2$ . TMED

| Carrier Gas = Nitrogen Sample Wt. 22.75 mg | | Carrier Gas = Air Sample Wt. 19.6 mg | |
|---|---|---|---|
| Temp./ (°C.) | Wt. % Volatilized | Temp. (°C.) | Wt. % Volatilized |
| 135 | 0 | 125 | 0 |
| 150 | 0.7 | 150 | 0.5 |
| 160 | 1.1 | 175 | 3.1 |
| 170 | 2.2 | 185 | 5.1 |
| 175 | 3.3 | 200 | 11.1 |
| 180 | 4.4 | 210 | 18.4 |
| 190 | 7.7 | 215 | 23.5 |
| 200 | 13.2 | 225 | 36.7 |
| 205 | 16.5 | 230 | 43.9 |
| 210 | 20.4 | 235 | 57.1 |
| 215 | 25.7 | 240 | 73.5 |
| 225 | 38.0 | 244 | 89.8 |
| 235 | 52.7 | 245 | 92.9 |
| 240 | 62.6 | 246 | 96.9 |
| 245 | 78.0 | 250 | 97.4 |
| 250 | 98.7 | | |

EXAMPLE 5

Preparation of Bis(acetylacetonato)Ni(II)tetramethylethylenediamine, Ni(II)(AA)$_2$.TMED, wherein $R_1$=$R_2$=CH$_3$; $R_3$=H; $R_4$=$R_5$=CH$_3$; and A=—CH$_2$—CH$_2$—.

In a 2-liter reaction flask equipped with an agitator, a thermometer, a condenser and an addition funnel, 30 g of acetylacetone (AA) and 375 ml of deionized water were stirred for 10 minutes. To the mixture was added a solution of 12.25 g of sodium hydroxide in 37.5 ml of deionized water over 7 minutes, resulting in a light yellow solution. After stirring for 15 minutes, a solution of 35.7 g of NiCl$_2$.6H$_2$O dissolved in 150 ml of deionized water was added over 17 minutes. There was no temperature rise and a bluegreen precipitate formed. After stirring for 1 hour, 17.4 g of tetramethylethylenediamine (TMED) was added over 7 minutes. After stirring for 2½ hours, the reaction mixture was filtered and washed with water. Partially dried cake was dissolved in 175 ml of toluene and filtered. Removal of toluene at 45° to 50° C. under reduced pressure yielded 42 g (75% yield) of blue solid, m.p. 98.5° C.

Elemental analysis: Calculated for Ni($C_{16}H_{30}N_2O_4$): C, 51.5; H, 8.1; N, 7.5; Ni, 15.7. Found: C, 51.4; H, 7.7; N, 7.7; Ni, 15.7.

| Thermogravimetric Analysis Ni(II) (AA)$_2$ . TMED | | | |
|---|---|---|---|
| Carrier Gas = Nitrogen Sample Wt. 16.8 mg | | Carrier Gas = Air Sample Wt. 19.6 mg | |
| Temp. (°C.) | Wt. % Volatilized | Temp. (°C.) | Wt. % Volatilized |
| 100 | 0 | 100 | 0 |
| 115 | 1.2 | 110 | 0.5 |
| 125 | 2.4 | 120 | 2.0 |
| 140 | 7.1 | 125 | 3.1 |
| 150 | 11.9 | 135 | 6.1 |
| 160 | 17.9 | 140 | 8.2 |
| 170 | 25.0 | 150 | 12.2 |
| 180 | 35.7 | 160 | 18.4 |
| 190 | 50.0 | 165 | 21.4 |
| 200 | 69.0 | 170 | 25.5 |
| 205 | 79.8 | 175 | 30.6 |
| 210 | 89.3 | 185 | 42.4 |
| 214 | 94.0 | 195 | 59.2 |
| 225 | 95.2 | 200 | 69.4 |
| | | 205 | 79.6 |
| | | 207 | 84.7 |
| | | 211 | 89.8 |
| | | 213 | 90.8 |
| | | 225 | 91.8 |

EXAMPLE 6

Preparation of Bis(acetylacetonato)Fe(II)tetramethylethylenediamine, Fe(II)(AA)$_2$.TMED, wherein $R_1=R_2=CH_3$; $R_3=H$; $R_4=R_5=CH_3$; and A=—$CH_2$—$CH_2$—.

In a 250 ml reaction flask equipped with an agitator, a thermometer, a condenser and an addition funnel, a mixture of 9.9 g of FeCl$_2$.4H$_2$O and 50 ml of water was stirred. To the mixture a solution of 5.8 g of N,N,N',N'-tetramethylethylenediamine (TMED) in 10.0 g of acetylacetone (AA) was added over 30 minutes causing a temperature rise of 9° C. and the formation of a reddish-brown precipitate. After stirring for 30 minutes, a solution of 4.1 g of sodium hydroxide in 12.5 ml of water was added over 20 minutes, the temperature rising 3° C. and the precipitate turning brick-red. After stirring 1½ hours, the reaction mass was filtered and the precipitate was washed with water. The partially dry cake was dissolved in 325 ml of toluene and filtered. Removal of toluene at 50° C. under reduced pressure provided 4.4 g of bright red solid, m.p. 187° to 188° C. Elemental analysis: Calculated for Fe($C_{16}H_{30}N_2O_4$): C, 51.9; H, 8.2; N, 7.6; Fe, 15.1. Found: C, 51.0; H, 5.8; N, 5.3; Fe, 14.5.

EXAMPLE 7

Preparation of Bis(dipivaloyolmethane)Mn(II)tetramethylethylenediamine, Mn(II)(DPM)$_2$.TMED, wherein $R_1=R_2=C(CH_3)$; $R_3=H$; $R_4=R_5=CH_3$; A=—$CH_2$—$CH_2$—.

In a 500 ml reaction flask equipped with an agitator, a thermometer, a condenser and an addition funnel, 50 ml of denatured ethyl alcohol (2% benzene) and 9.9 g of MnCl$_2$.4H$_2$O was stirred under a nitrogen atmosphere. To the above mixture, a solution of 6.5 g of N,N,N',N'-tetramethylpropylenediamine (TMPD) in 18.4 g dipivaloylmethane (DPM) was added over a period of 20 minutes causing a temperature rise of about 3° C. and the formation of yellow precipitates. After stirring for about 30 minutes, a solution of 4.1 g of sodium hydroxide in 12.5 ml of water was added over a period of 17 minutes, the temperature rising an additional 5° C. The mixture was stirred for 1½ hours, filtered, and the precipitate was washed with water. The partially dried cake was dissolved in 200 ml of toluene and filtered. Removal of toluene at 40° to 50° C. under partial vacuum yielded 20.4 g (74% yield) of light greenish-yellow solid (m.p. 177° C.). Elemental analysis: Calculated for Mn($C_{28}H_{54}N_2O_4$): C, 62.6; H, 10.1; N, 5.2; Mn, 10.2. Found: C, 62.6; H, 10.0; N, 4.5; Mn, 9.7.

| Thermogravimetric Analysis Mn(II) (DPM)$_2$ . TMED | | | |
|---|---|---|---|
| Carrier Gas = Nitrogen Sample Wt. 18.9 mg | | Carrier Gas = Air Sample Wt. 19.6 mg | |
| Temp. (°C.) | Wt. % Volatilized | Temp. (°C.) | Wt. % Volatilized |
| 135 | 0 | 125 | 0 |
| 145 | 0.5 | 150 | 0.5 |
| 155 | 1.1 | 163 | 2.0 |
| 165 | 1.6 | 175 | 4.6 |
| 170 | 2.6 | 195 | 14.3 |
| 175 | 3.7 | 200 | 19.4 |
| 180 | 5.3 | 210 | 31.6 |
| 190 | 9.0 | 215 | 38.8 |
| 200 | 16.4 | 225 | 54.1 |
| 210 | 25.9 | 230 | 63.8 |
| 217 | 36.5 | 235 | 72.4 |
| 225 | 48.7 | 240 | 79.6 |
| 230 | 57.7 | 245 | 86.7 |
| 235 | 68.2 | 250 | 91.8 |
| 240 | 78.8 | 255 | 93.7 |
| 245 | 87.3 | 257 | 94.9 |
| 250 Decomposition | 92.6 | Decomposition | |

EXAMPLE 8

Preparation of Bis(benzoylacetonato)Mn(II)tetramethylethylenediamine, Mn(II)(BA)$_2$.TMED, wherein $R_1=CH_3$; $R_2=C_6H_5$; $R_3=H$; $R_4=R_5=CH_3$; A=—$CH_2$—$CH_2$—.

In a 250 ml reaction flask equipped with an agitator, a thermometer, a condenser and an addition funnel, was stirred 9.9 g of MnCl$_2$.4H$_2$O and 50 ml of denatured ethyl alcohol. To the mixture 16.2 g of benzoylacetone, (BA), was added to form a yellow suspension. To the mixture was added 6 g of N,N,N',N'-tetramethylethylenediamine (TMED) and the suspension changed to yellowish-orange and the temperature rose 7° C. After stirring for 1½ hours, a solution of 4.1 g of sodium hydroxide in 12.5 ml of water was added over 10 minutes. The mixture was stirred for an additional 1½ hours and filtered. The filter cake was washed with water until free of alkali. The partially dried cake was dissolved in 320 ml of toluene and the toluene solution was filtered. Removal of toluene at 50° to 55° C. at reduced pressure yielded 22 g (92% theory) of dark yellow solid. Elemental analysis: Calculated for Mn($C_{26}H_{34}N_2O_4$): C, 63.3; H, 6.9; N, 5.7; Mn, 11.1. Found: C, 63.8; H, 6.6; N, 5.7; Mn, 11.2.

EXAMPLE 9

Preparation of Bis(dipivaloylmethanato)Mn(II)tetramethylethylenediamine, Mn(II)(DPM)$_2$.TMED, wherein $R_1=R_2=C(CH_3)_3$; $R_3=H$; $R_4=R_5=CH_3$; A=—$CH_2$—$CH_2$—.

Into a 250 ml reaction flask equipped with an agitator, a thermometer, a condenser and an addition funnel, was added 50 ml of denatured ethyl alcohol and 9.9 g of MnCl$_2$.4H$_2$O. The mixture was stirred and a solution of 18.4 g of 2,2,6,6-tetramethyl-3,5-heptanedione (dipivaloylmethane, DPM) and 5.8 g of N,N,N',N'-tetramethylethylenediamine (TMED) was added over 45 minutes (temperature rise 6° C.) resulting in the formation of a dark brown precipitate. The mixture was stirred for ½ hour and a solution of 4 g of sodium hydroxide in 12.5 ml of water was added over 35 minutes (temperature rise 6° C.). The precipitate changed to dark green. The reaction mixture was stirred for an additional 1½ hours and filtered. The precipitate was washed with water until neutral. The product was dried in a vacuum desiccator to yield 24 g of dark green solid. Twelve grams of the product was dissolved in 80 ml of toluene and the toluene solution was filtered. Removal of the toluene under reduced pressure provided 11.4 g of greenish-yellow solid. Elemental analysis: Calculated for $Mn(C_{28}H_{54}N_2O_4)$: C, 62.6; H, 10.1; N, 5.2; Mn, 10.2. Found: C, 62.9; H, 10.0; N, 4.7; Mn, 10.1.

Note: An attempt to prepare $Mn(II)(DPM)_2 \cdot 2N(CH_3)_3$ by using trimethylamine in place of tetramethylethylenediamine was not successful, no isolatable compound being formed. Tetramethylethylenediamine, $(CH_3)_2N-CH_2CH_2N(CH_3)_2$, differs from trimethylamine, $(CH_3)_2NCH_3$, in that the two amino groups are joined through two methylene groups. It was concluded from the unsuccessful attempts to make $Mn(II)(DPM)_2 \cdot 2N(CH_3)_3$ that the two amino groups should be connected via two or three carbon atoms to provide sufficiently stable compounds.

EXAMPLES 10 TO 14

Using the procedure substantially as described in Example 9, the following bis(dipivaloylmethanato)Mn(II)diamine coordination compounds were prepared by using the indicated diamine ligands in place of tetramethylethylenediamine.

EXAMPLE 10

| Diamine | Compound |
| --- | --- |
| Ethylenediamine (ED) wherein: $R_1 = R_2 = C(CH_3)_3$ $R_3 = H$ $R_4 = R_5 = H$ $A = -CH_2-CH_2-$ | $Mn(II) (DPM)_2 \cdot ED$ |

EXAMPLE 11

| Diamine | Compound |
| --- | --- |
| Unsym.-dimethylethylenediamine (u-DMED) wherein: $R_1 = R_2 = C(CH_3)_3$ $R_3 = H$ $R_4$ on first N = $CH_3$; $R_4$ on second N = H $R_5$ on first N = $CH_3$; $R_5$ on second N = H $A = -CH_2CH_2-$. | $Mn(II) (DPM)_2 \cdot u\text{-DMED}$ |

EXAMPLE 12

| Diamine | Compound |
| --- | --- |
| Sym.-dimethylethylenediamine (s-DMED) wherein: $R_1 = R_2 = C(CH_3)_3$ $R_3 = H$ $R_4 = CH_3$ $R_5 = H$ $A = -CH_2-CH_2-$ | $Mn(II) (DPM)_2 \cdot s\text{-DMED}$ |

EXAMPLE 13

| Diamine | Compound |
| --- | --- |
| 4,5-Dimethyl-o-phenylenediamine (DMOPD) wherein: $R_1 = R_2 = C(CH_3)_3$ $R_3 = H$ $R_4 = R_5 = H$ $A = $ -4,5-dimethyl-o-phenylene- | $Mn(II) (DPM)_2 \cdot DMOPD$ |

EXAMPLE 14

| Diamine | Compound |
| --- | --- |
| N,N,N',N'-tetramethyl-o-phenylenediamine (TMOPD) wherein: $R_1 = R_2 = C(CH_3)_3$ $R_3 = H$ $R_4 = R_5 = CH_3$ $A = $ -o-phenylene- | $Mn(II) (DPM)_2 \cdot TMOPD$ |

Each of the above compounds was stable in air and soluble in hydrocarbons. Gasoline solutions of the above compounds under nitrogen atmosphere were stable; however, on exposure to air, slow oxidation was observed.

EXAMPLES 15 to 49

The utility of the compounds of this invention as antiknock additives in gasoline is demonstrated in these Examples. The octane numbers of the gasoline containing the compounds were determined by the Research Method (ASTM D-909) and the Motor Method (ASTM D-357). The compounds were added to the base gasoline to provide the indicated concentration of the metal per gallon of gasoline. The base gasoline was commercial lead-free gasoline having the following inspection data:

| Base Fuel | |
| --- | --- |
| Hydrocarbon Types (ASTM D-1319) | |
| Saturated hydrocarbons, volume percent | 61 |
| Olefinic hydrocarbons, volume percent | 8 |
| Aromatic hydrocarbons, volume percent | 31 |
| Distillation (ASTM D-86) | °C. |
|  | (nearest whole °) |
| Initial Boiling Point | 38 |
| 5% | 53 |
| 10% | 62 |
| 20% | 82 |
| 30% | 97 |
| 40% | 111 |
| 50% | 122 |
| 60% | 132 |
| 70% | 144 |
| 80% | 159 |
| 90% | 179 |
| 95% | 201 |
| Max. Temp. | 219 |
| Recovery, volume percent | 98 |

-continued

| Base Fuel | |
|---|---|
| Residue, volume percent | 1 |
| Gravity (ASTM D-287) | |
| Degree API | 56.1 |
| lbs/gal | 6.279 |
| Specific 60/60F | 0.754 |
| Vapor Pressure (Reid) (ASTM D-323) lbs | 7.9 |
| Induction Period (ASTM D-525) | No ASTM Break |
| % sulfur (ASTM D-3120), weight percent | 0.034 |
| Mercaptan sulfur, weight percent (ASTM D-1323) | 0.0004 |

The fuel samples were knock-rated in duplicate by two different operators employing the standard technique. The results reported herein are averages of these ratings.

It will be noted that each of the cobalt and nickel compounds is an excellent antiknock additive providing octane number increase ($\Delta ON$) of about 2.5 at the metal concentration of 0.3 g per gallon. The manganese compound, $Mn(II) (DPM)_2 \cdot TMED$, is less effective on the metal weight basis. The gasoline solution of the manganese compound deposited some precipitate after about 10 days, indicating a lesser degree of oxidative stability compared to the cobalt and nickel compounds. The decreased efficiency as an antiknock additive may be due to the lesser oxidative stability of the manganese compound since some of the compound may undergo oxidative decomposition in the intake manifold of the engine and thus would not be available to exert its antiknock activity in the combustion chamber.

Antiknock Performance
$Co(II) (AA)_2 \cdot TMED$

| | | Octane Numbers (ON) | | | |
|---|---|---|---|---|---|
| | | Research | | Motor | |
| Example | gm metal/gallon | ON | 66 ON | ON | $\Delta ON$ |
| | Base fuel | 91.38 | — | 82.01 | — |
| 15 | 0.025 | 91.58 | 0.20 | 82.05 | 0.04 |
| 16 | 0.05 | 92.31 | 0.93 | 82.27 | 0.26 |
| 17 | 0.10 | 92.88 | 1.50 | 82.50 | 0.49 |
| 18 | 0.15 | 93.12 | 1.74 | 82.68 | 0.67 |
| 19 | 0.20 | 93.46 | 2.08 | 82.75 | 0.74 |
| 20 | 0.25 | 93.51 | 2.13 | 82.77 | 0.76 |
| 21 | 0.30 | 93.79 | 2.41 | 82.99 | 0.98 |

Antiknock Performance
$Co(II) (DPM)_2 \cdot TMED$

| | | Octane Numbers (ON) | | | |
|---|---|---|---|---|---|
| | | Research | | Motor | |
| Example | gm metal/gallon | ON | $\Delta ON$ | ON | $\Delta ON$ |
| | Base fuel | 91.30 | — | 81.99 | — |
| 22 | 0.025 | 91.94 | 0.64 | 82.26 | 0.27 |
| 23 | 0.05 | 92.81 | 1.51 | 82.67 | 0.68 |
| 24 | 0.10 | 93.20 | 1.90 | 83.17 | 1.18 |
| 25 | 0.15 | 93.52 | 2.22 | 83.41 | 1.42 |
| 26 | 0.20 | 93.86 | 2.56 | 83.56 | 1.57 |
| 27 | 0.25 | 94.11 | 2.81 | 83.85 | 1.86 |
| 28 | 0.30 | 93.94 | 2.64 | 83.86 | 1.87 |

Antiknock Performance
$Co(II) (IVA)_2 \cdot TMED$

| | | Octane Numbers (ON) | | | |
|---|---|---|---|---|---|
| | | Research | | Motor | |
| Example | gm metal/gallon | ON | $\Delta ON$ | ON | $\Delta ON$ |
| | Base fuel | 91.63 | — | 82.22 | — |
| 29 | 0.025 | 92.26 | 0.63 | 82.56 | 0.34 |
| 30 | 0.05 | 92.77 | 1.14 | 82.72 | 0.50 |
| 31 | 0.10 | 93.42 | 1.79 | 82.99 | 0.77 |
| 32 | 0.15 | 93.59 | 1.96 | 83.08 | 0.86 |
| 33 | 0.20 | 93.56 | 1.93 | 83.09 | 0.87 |
| 34 | 0.25 | 93.86 | 2.23 | 83.26 | 1.04 |
| 35 | 0.30 | 94.06 | 2.43 | 83.44 | 1.22 |

Antiknock Performance
$Ni(II) (AA)_2 \cdot TMED$

| | | Octane Number (ON) | | | |
|---|---|---|---|---|---|
| | | Research | | Motor | |
| Example | gm metal/gallon | ON | $\Delta ON$ | ON | $\Delta ON$ |
| | Base fuel | 91.10 | — | 82.77 | — |
| 36 | 0.025 | 91.24 | 0.14 | 83.06 | 0.29 |
| 37 | 0.05 | 91.50 | 0.40 | 83.10 | 0.33 |
| 38 | 0.10 | 92.38 | 1.28 | 83.33 | 0.56 |
| 39 | 0.15 | 93.00 | 1.90 | 83.50 | 0.73 |
| 40 | 0.20 | 93.40 | 2.30 | 83.76 | 0.99 |
| 41 | 0.25 | 93.58 | 2.48 | 84.07 | 1.30 |
| 42 | 0.30 | 93.63 | 2.53 | 84.37 | 1.60 |

Antiknock Performance
$Mn(II) (DPM)_2 \cdot TMED$

| | | Octane Numbers (ON) | | | |
|---|---|---|---|---|---|
| | | Research | | Motor | |
| Example | gm metal/gallon | ON | $\Delta ON$ | ON | $\Delta ON$ |
| | Base fuel | 91.54 | — | 81.89 | — |
| 43 | 0.025 | 91.61 | 0.07 | 81.98 | 0.09 |
| 44 | 0.05 | 92.00 | 0.46 | 82.58 | 0.69 |
| 45 | 0.10 | 92.36 | 0.82 | 82.65 | 0.76 |
| 46 | 0.15 | 92.46 | 0.92 | 82.24 | 0.35 |
| 47 | 0.20 | 92.48 | 0.94 | 82.18 | 0.29 |
| 48 | 0.25 | 92.45 | 0.91 | 82.24 | 0.35 |
| 49 | 0.30 | 92.56 | 1.02 | 82.20 | 0.31 |

EXAMPLES 50 to 58

In another series, the antiknock performance of $Co(II) (AA)_2 \cdot TMED$ was determined using a modified Research Octane Number Method. The modification consisted of using fuel injection in place of the usual carburetion, all other conditions remaining the same. In this modification, fuel is injected directly into the combustion chamber.

| Base Fuel | |
|---|---|
| Composition: | |
| Saturated hydrocarbons, volume percent | 65 |
| Olefinic hydrocarbons, volume percent | 9 |
| Aromatic hydrocarbons, volume percent | 26 |
| Distillation: | °C. (nearest whole°) |
| Initial Boiling Point | 41 |
| 10% | 59 |
| 50% | 94 |
| 90% | 154 |
| Max. Temp. | 177 |
| Recovery, volume percent | 97 |
| Residue, volume percent | 1 |
| Reid Vapor Pressure, lb | 8.6 |

-continued

| Base Fuel | |
|---|---|
| Sulfur, weight percent | 0.002 |

Antiknock Performance
$Co(II)(AA)_2 \cdot TMED$
Modified Fuel Injection Research Method

| | | Octane Numbers | |
|---|---|---|---|
| Example | gm metal/gallon | ON | ΔON |
| Base fuel | | 91.1 | — |
| 50 | 0.10 | 93.1 | 2.0 |
| 51 | 0.25 | 93.7 | 2.8 |
| 52 | 0.50 | 95.0 | 3.9 |
| 53 | 0.75 | 95.8 | 4.7 |
| 54 | 1.00 | 96.6 | 5.5 |
| 55 | 1.50 | 97.6 | 6.5 |
| 56 | 2.00 | 98.6 | 7.5 |
| 57 | 2.50 | 100.2 | 9.1 |
| 58 | 3.00 | 101.6 | 10.5 |

EXAMPLES 59 to 76

The utility of the hexacoordinated compounds of this invention as antiknock additives in gasoline was further demonstrated in Road Octane tests carried out according to the Modified Uniontown Method (CRC F-28-70). For these tests, a fleet of 8 automobiles identified as follows was used:

| | Trans-mission | Engine | | | | |
|---|---|---|---|---|---|---|
| | | No. Cyl. | Comp. Ratio | Displ. cu in | Brake Horse-power | Carb. bbl |
| 1975 Buick Electra 225 | Auto | 8 | 7.9 | 455 | 210 | 4 |
| 1975 Chevrolet | Auto | 8 | 8.5 | 350 | 145 | 2 |
| 1976 Ford Granada | Auto | 8 | 8.0 | 302 | 129 | 2 |
| 1975 Pontiac Catalina | Auto | 8 | 7.6 | 400 | 170 | 2 |
| 1976 Plymouth Valiant | Auto | 6 | 8.4 | 225 | 95 | 1 |
| 1976 Ford Pinto | Auto | 4 | 9.0 | 140 | 83 | 1 |
| 1976 Chevrolet Chevette | Auto | 4 | 8.5 | 98 | 60 | 1 |
| 1976 Chevrolet Chevette | Man. | 4 | 8.5 | 98 | 60 | 1 |

The gasoline used was industry-known lead-free Indolene having the following characteristics:

| Base Fuel | |
|---|---|
| Hydrocarbon Types (ASTM D-1319) | |
| Saturated hydrocarbons, volume percent | 73 |
| Olefinic hydrocarbons, volume percent | 3 |
| Aromatic hydrocarbons, volume percent | 24 |
| Distillation (ASTM D-86) | °C. |
| | (to nearest whole °) |
| Initial Boiling Point | 33 |
| 5% | 44 |
| 50% | 109 |
| 95% | 188 |
| Max. Temp. | 202 |
| Sulfur, weight percent (ASTM D-3120) | 0.014 |
| Reid Vapor Pressure (ASTM D-323), lb | 9.9 |
| Base Fuel Road Octane Rating | 89.3 |

The ratings were carried out in triplicate and the average octane numbers for the 8 cars are summarized below in terms of increase in octane numbers (ΔON) over the octane number of the base fuel. The following data show that each of the compounds tested is an effective antiknock additive.

Road Antiknock Performance
Modified Uniontown Ratings
Base Fuel = Indolene
Base Fuel Road Octane Rating = 89.3

| Examples | gm metal/ gallon | Co(II) $(AA)_2 \cdot$ TMED | Co(II) $(IVA)_2 \cdot$ TMED | Co(II) $(DPM)_2 \cdot$ TMED |
|---|---|---|---|---|
| 59 to 61 | 0.025 | 0.36 | 0.31 | 0.24 |
| 62 to 64 | 0.05 | 0.56 | 0.73 | 0.39 |
| 65 to 67 | 0.10 | 0.87 | 1.03 | 0.69 |
| 68 to 70 | 0.15 | 1.17 | 1.37 | 1.10 |
| 71 to 73 | 0.20 | 1.42 | 1.62 | 1.46 |
| 74 to 76 | 0.25 | 1.58 | 1.79 | 1.61 |

The embodiments of the invention in which an exclusive property or privilege is claimed are defined as follows:

1. The hexacoordinated transition metal compound represented by the formula

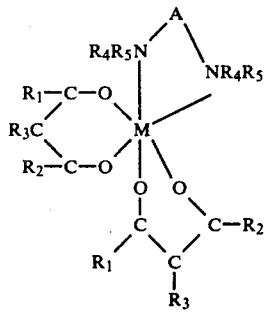

wherein:
M is selected from at least one member of the group Mn, Fe, Co and Ni,
$R_1$ and $R_2$ are hydrocarbyl groups of 1 to 6 carbon atoms,
$R_3$ is hydrogen or an alkyl of 1 to 6 carbon atoms,
$R_4$ and $R_5$ are hydrogen or alkyl of 1 to 4 carbon atoms, and
A is a divalent hydrocarbyl group of 2 to 10 carbon atoms selected from a member of the group alkylene, phenylene and cycloalkylene, each member providing 2 or 3 carbon atoms between the nitrogen atoms with the proviso that when A is phenylene the number of carbon atoms between the nitrogen atoms is 2.

2. The compound of claim 1 wherein M is selected from one of cobalt and nickel.
3. The compound of claim 2 wherein M is cobalt.
4. The compound of claim 1 wherein $R_1=R_2=CH_3$, $R_3=H$, $R_4=R_5=CH_3$ and A is $-CH_2-CH_2-$.
5. The compound of claim 1 wherein $R_1=CH_3$, $R_2=-CH_2CH(CH_3)_2$, $R_3=H$, $R_4=R_5=CH_3$ and A is $-CH_2CH_2-$.
6. The compound of claim 1 wherein $R_1=R_2=C(CH_3)_3$, $R_3=H$, $R_4=R_5=CH_3$ and A is $-CH_2CH_2-$.
7. The compound of claim 4 wherein M is Co.
8. The compound of claim 5 wherein M is Co.
9. The compound of claim 6 wherein M is Co.
10. The composition comprising hydrocarbons boiling in the gasoline boiling range and an octane-improving amount of the compound of claim 1.

* * * * *